United States Patent [19]

Varadarajan et al.

[11] Patent Number: 5,798,089
[45] Date of Patent: Aug. 25, 1998

[54] CHELANT MOIETIES LINKED TO AN ARYL MOIETY BY AN INTERRUPTED ALKYLENE LINKER

[75] Inventors: John Varadarajan; Alan David Watson, both of Wayne, Pa.; Arne Berg, Oslo, Norway

[73] Assignee: Nycomed Salutar, Inc., Wayne, Pa.

[21] Appl. No.: 727,594

[22] PCT Filed: Apr. 12, 1995

[86] PCT No.: PCT/GB95/00833

§ 371 Date: Jan. 17, 1997

§ 102(e) Date: Jan. 17, 1997

[87] PCT Pub. No.: WO95/28392

PCT Pub. Date: Oct. 26, 1995

[30] Foreign Application Priority Data

Apr. 14, 1994 [GB] United Kingdom ............... 9407435

[51] Int. Cl.$^6$ .................. A61K 51/04; A61B 5/055; C07D 257/02; C07D 225/00

[52] U.S. Cl. .................. 424/1.65; 424/9.36; 424/9.363; 424/9.361; 534/10; 534/14; 534/15; 534/16; 540/465; 540/474

[58] Field of Search .................. 424/1.65, 1.69, 424/9.36, 9.361, 9.363, 9.364; 534/10, 14, 15, 16; 540/465, 474; 514/184, 436

[56] References Cited

U.S. PATENT DOCUMENTS 5,410,043  4/1995  Platzek et al. ............... 540/465

FOREIGN PATENT DOCUMENTS 0 485 045  5/1992  European Pat. Off. .
0 588 229  3/1994  European Pat. Off. .
0 596 586  5/1994  European Pat. Off. .

Primary Examiner—Gary E. Hollinden
Assistant Examiner—Michael G. Hartley
Attorney, Agent, or Firm—Fish & Richardson P.C.

[57] ABSTRACT

The invention provides amphiphilic compounds of the formula (I) Ch—(—L—Ar—(—AH)$_n$)$_m$ (where Ch is a hydrophilic chelant moiety or a salt or a chelate thereof); each L is an optionally oxo substituted $C_{2-25}$-alkylene linker wherein at least one $CH_2$ moiety is replaced by a group $X^1$ (e.g. L may include a chain sequence, an $X^1(CH_2CH_2X^1)_u$ (where u is a positive integer) such as $X^1(CH_2CH_2X^1)_u$, $CH_2X^1CH_2CH_2X^1CH_2CH_2X^1$, $CH_2X^1CH_2CH_2X^1CH_2CH_2X^1CH_2CH_2X^1$, etc.), and wherein L is optionally interrupted by a metabolizable group M but with the provisos that the terminus of L adjacent Ch is $CH_2$ and that the terminus of L adjacent Ar is $X^1$ or a $CH_2$ group adjacent or separated by one $CH_2$ from a group $X^1$ (thus, for example the L—Ar linkage may be $L^1$—$X^1$—Ar, $L^1$—$CH_2$—Ar, $L^1$—$X^1CH_2$—Ar or $L^1$—$X^1CH_2CH_2$—Ar, where $L^1$ is the residue of L; each Ar is an aryl ring optionally substituted by or having fused thereto a further aryl ring; each AH is a protic acid group, preferably an oxyacid, e.g. a carbon, sulphur or phosphorus oxyacid or a salt thereof; each $X^1$ is O, S, $NR^1$ or $PR^1$, preferably no more than 3 $X^1$ groups being present in L; each $R^1$ is hydrogen, alkyl or aryl; and m and n are positive integers, m being for example 1 to 4, especially 1 or 2 and n being for example, 1, 2 or 3) which are especially suited for use in diagnostic imaging of the hepatobiliary system.

17 Claims, 2 Drawing Sheets

FIG. 1

DO3A-DOBA

FIG. 2

CHELANT MOIETIES LINKED TO AN ARYL MOIETY BY AN INTERRUPTED ALKYLENE LINKER

The invention relates to novel amphiphilic chelants to the chelates and salts thereof and particularly to their use as diagnostic image contrast enhancing agents.

It is well accepted in diagnostic imaging modalities, such as magnetic resonance imaging, X-ray imaging, scintigraphy, ultrasound and the like, that the use of contrast agents can lead to improved image contrast and higher diagnostic efficacy.

A large proportion of contrast agents that have been developed for imaging other than of the gut, have been extracellular agents which after injection leave the vascular space and are excreted by the kidneys by glomerular filtration. However in order to obtain diagnostically useful information of other organs it is desirable to develop target specific contrast agents which distribute preferentially to the desired target site and remain there for a time sufficient for image generation to be effected.

Among the primary internal organs, the liver plays a leading role in the processing and metabolising of toxins, particulates and macromolecules as well as being involved in the absorption and digestion of fat. Processed materials are released through the biliary system and finally excreted. The detection of both focal and diffuse liver diseases such as primary and metastatic cancers is thus of great importance and the development of contrast agents for the liver has received much attention (see Schuhmann-Giampieri, Invest. Radiol. 28: 753–761 (1993)).

To image the liver using contrast agents, three main approaches have been adopted. The first is simply to target the blood passing through the liver using ECF agents and fast imaging procedures or MRI blood pool agents, the second is to target the Kupffer cells of the reticuloendothelial system in the liver, and the third is to target the hepatocytes, the cells which account for over 90% of the liver.

The present invention is concerned with liver targeting contrast agents.

For MR imaging, paramagnetic metal chelate hepatobiliary agents such as Gd-EOB-DTPA and MnDPDP are under development by Schering and Nycomed Salutar respectively. The paramagnetic MRI imaging agent GdBOPTA has also been proposed for liver imaging by Bracco and arabinogalactan-coated ultrasmall superparamagnetic iron oxide (AG-USPTO) particles have been proposed by Advanced Magnetics.

Besides the normal concerns in relation to toxicity, a requirement for a hepatobiliary contrast agent to function adequately is that liver uptake should occur efficiently and that retention within the hepatobiliary system in a contrast inducing form should be for an adequate period for imaging to be effected.

It has now been found that surprisingly good liver uptake and prolonged hepatobiliary system retention is achieved with novel amphiphilic contrast agents comprising a chelate conjugated to an acid group carrying aryl function.

Figure 2:
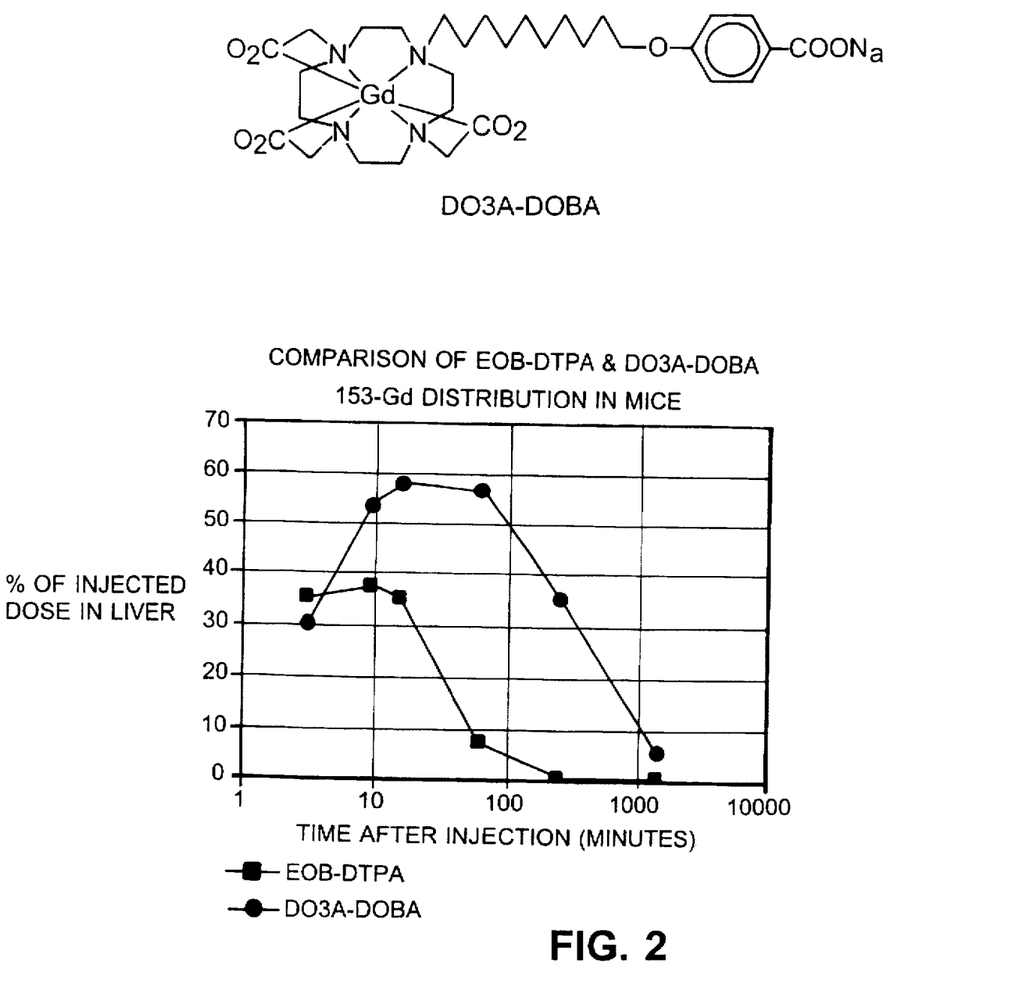
FIG. 2 is a comparative plot of the pattern of distribution to the mouse liver of a compound according to the invention and of GdEOB-DTPA, a prior art liver agent.

By way of example, one such chelate Gd-DO3A-DOBA (10-p-carboxyphenoxydecyl-1,4,7,10-tetraazacyclododecane-1,4,7-tri-acetic acid) achieves a significantly higher and more prolonged accumulation in the liver than does Gd-EOB-DTPA as may be seen from FIG. 2 of the accompanying drawings.

Thus viewed from one aspect the invention provides an amphiphilic compound of formula I $$Ch(-L-Ar(-AH)_n)_m \qquad (I)$$

(where Ch is a hydrophilic chelant moiety or a salt or a chelate thereof;

each L is an optionally oxo substituted $C_{2-25}$-alkylene linker wherein at least one $CH_2$ moiety is replaced by a group $X^1$ (e.g. L may include a chain sequence, a $X^1(CH_2CH_2X^1)_u$ (where u is a positive integer) such as $X^1CH_2CH_2X^1$, $X^1CH_2CH_2X^1CH_2CH_2X^1$, $X^1CH_2CH_2X^1CH_2CH_2X^1CH_2CH_2X^1$, etc), and wherein L is optionally interrupted by a metabolizable group M but with the provisos that the terminus of L adjacent Ch is $CH_2$ and that the terminus of L adjacent Ar is $X^1$ or a $CH_2$ group adjacent or separated by one $CH_2$ from a group $X^1$ (thus for example the L—Ar linkage may be $L^1-X^1-Ar$, $L^1-CH_2-Ar$, $L^1-X^1CH_2-Ar$ or $L^1-X^1CH_2CH_2-Ar$, where $L^1$ is the residue of L);

each Ar is an aryl ring optionally substituted by or having fused thereto a further aryl ring;

each AH is a protic acid group, preferably an oxyacid, e.g. a carbon, sulphur or phosphorus oxyacid or a salt thereof;

each $X^1$ is O, S, $NR^1$ or $PR^1$, preferably no more than 3 $X^1$ groups being present in L;

each $R^1$ is hydrogen, alkyl or aryl;

m and n are positive integers, m being for example 1 to 4, especially 1 or 2 and n being for example 1, 2 or 3).

The chelant moiety may be any of the chelants proposed in the literature that tightly binds lanthanides.

The chelant moiety may be an acyclic chelant, in particular an aminopolycarboxylic acid (APCA) chelant or a phosphorus oxyacid analogue thereof, e.g. DTPA, TTHA, PLED and DPDP. However, it is preferred that the chelant be a macrocyclic chelant, e.g. DO3A. In particular, the chelant moiety may be any of those proposed in particular in the Patent applications of Schering, Nycomed Imaging, Nycomed Salutar, Bracco, Squibb, Mallinckrodt and Guerbet relating to MR contrast agents and preferably is a group of formula where each $X^2$ is O, S or $NR^3$, preferably each being $NR^3$;

each $R^2$ is a bond to a group L, a hydrogen atom or a hydroxyalkyl group, preferably each $(CR^2{}_2)_p$ moiety containing no more than one non-hydrogen $R^2$;

each $R^3$ is a hydroxyalkyl group, a group $CR^4AH$, a group $CHAR^4$ or a bond to a group L, at least two, preferably 3 and particularly preferably all except one $R^3$ being groups $CR^4AH$;

each $R^4$ is a hydrogen atom or a bond to a group L;

each p is 1, 2, 3 or 4, preferably 2;

q is 3 to 8, preferably 4;

v is 0 to 6, preferably 0, 1, 2 or 3;

and at least one $R^2$, $R^3$ or $R^4$ is a bond to a group L. Particularly preferred macrocyclic skeletons include -continued and especially Especially preferred as-chelant groups Ch are those of formulae where $R^4$ and AH are as hereinbefore defined, at least one $R^4$ is a bond to a linker group L, preferably with 3 or 4 $R^4$ groups being hydrogen and each AH being a group $CO_2H$, $SO_3H$, $PO_3H_2$ or $PO_2H$, and each Am group is an amide, or a salt or chelate thereof.

Where the aryl group Ar is monocyclic and the linker group L to which it is attached is a chain $(CH_2)_sX^1$, optionally attached to Ch via a $CH_2CONR^1$ group, then s is preferably at least 6, e.g. 7 to 15, particularly 8 to 12. Alternative preferred linker groups for monocyclic Ar groups include chains interrupted by metabolizable groups M and groups having repeating $X^1(CH_2)_t$ units (where t is 1, 2 or 3, preferably 2).

For bicyclic Ar groups, i.e. groups having an aryl ring bearing a further aryl ring as a substituent or groups having two fused aryl rings, the chain L is preferably a 2 to 20, particularly 2 to 16 atom chain, terminating at one end with $CH_2$ and at the other with a group $X^1$, optionally interrupted by a metabolizable group M, e.g. a $(CH_2)_a(M)_b(CH_2)_cX^1$ chain where a is 1 to 9, b is 0 or 1, and c is 1 to 10, preferably where a is 1 to 9, b is 0 and c is 1.

Examples of metabolizable groups M with which L may be interrupted include amide, ester, carbamate, acetal, ketal, disulfide, esters of phosphorus and sulfur oxyacids and carbonate.

Thus examples of preferred linker chain structures include

—$(CH_2)_dX^1$— wherein d is 1 to 15 where Ar is bicyclic and 7 to 15 where Ar is monocyclic —$CH_2CH_2$—$(X^1CH_2CH_2)_e$— where e is 1 to 6

—$(CH_2CH_2X^1)_h$— where h is 2 to 7

—$(CH_2)_gCONH(CH_2)_fX^1$— where f is 1 to 12 and g is 1 to 4

—$(CH_2)_gCOONH(CH_2)_fX^1$

—$(CH_2)_g$—$O(CO)O(CH_2)_fX^1$

—$(CH_2)_gCOO(CH_2)_fX^1$

—$(CH_2)_gNHCO(CH_2)_fX^1$

—$(CH_2)_gNHOCO(CH_2)_fX^1$

—$(CH_2)_gOCO(CH_2)_fX^1$

—$(CH_2)_gOCR^1HO(CH_2)_fX^1$

—$(CH_2)_gOCR^1_2O(CH_2)_fX^1$ and the analogous groups linked to the chelant Ch by a $CH_2CONR^1$ moieity, ie.

—$CH_2CONR^1(CH_2)_dX^1$—

—$CH_2$—$CONR^1CH_2CH_2(X^1CH_2CH_2)_e$—, etc.

In the above g is preferably 1 or 2 and f is preferably 1 to 10, e.g. 2 to 5.

Attachment of the linker L via a $CH_2CONR^1$ group (ie. incorporation of an amide M group at a position β to the Ch group) offers particular-advantages. In particular the amide oxygen can take part in complexing metal ions with which Ch is metallated so stabilizing the metal ion binding and leading to greater kinetic and thermodynamic stability.

The aryl groups, both in Ar and in substituents such as $R^1$, are carbocyclic or heterocyclic, in the latter case incorporating one or more heteroatoms selected from O, N, P and S, each ring preferably having 5 to 7 members but especially preferably each ring being $C_6$ carbocyclic.

Preferred bicyclic groups thus include biphenyl and napthalenyl groups, especially 4-biphenyl and 2-napthalenyl groups.

The protic AH groups present on the Ar groups and also on Ch groups are preferably carbon, sulphur or phosphorus oxyacid groups such as COOH, $SO_3H$, $PO_3H_2$ and $PO_2H$.

For monocyclic Ar groups, e.g. phenyl Ar groups, one AH group is preferably attached at a position remote from the point of attachment to linker L (i.e. the 3 or 4 position for phenyl Ar groups) with a further AH group optionally being attached at another position, e.g. to provide 2, 4, 3, 5 or 3, 4 disubstitution on a phenyl Ar group.

For bicyclic Ar groups, e.g. biphenyl and napthalenyl Ar groups, the AH groups, preferably one, two or three AH groups, may be attached to either or both of the rings.

Where the compounds of the invention are to be used as diagnostic agents, rather than in the preparation of such agents, the chelant moiety is metallated with a diagnostically useful metal ion.

Metal ions for chelation are chosen for their ability to perform their diagnostic or therapeutic role. These roles include but are not limited to enhancing images in MRI, gamma scintigraphic or CT scanning, or X-ray, or delivering cytotoxic agents to kill undesirable cells such as in tumors.

Metals that can be incorporated, through chelation, include transition metal ions, lanthanide ions and other metal ions, including isotopes and radioisotopes thereof, such as, for example, Mg, Ca, Sc, Ti, B, V, Cr, Mn, Fe, Co, Ni, Cu, Zn, Ga, Sr, Y, Zr, Tc, Ru, In, Hf, W, Re, Os, Pb and Bi. Particularly preferred radioisotopes of some of the foregoing include $^{153}$Sm, $^{64}$Cu, $^{67}$cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi, and $^{214}$Bi. The choice of metal ion for chelation by chelants of the invention will be determined by the desired therapeutic or diagnostic application.

For MRI, the metal ions should be paramagnetic, and preferably non-radioactive, with Dy, Gd, Fe, Mn and Cr being particularly preferred. For X-ray and ultrasound imaging, heavy metal ions, e.g. with atomic numbers of at least 37, preferably at least 50, should be used, again preferably non-radioactive species, with Hf, Ta, Re, Bi, W, Pb, Ba and Mo being especially preferred. Heavy metal cluster ions, e.g. polyoxoanions or partial or full sulphur analog may also be used. For scintigraphy or radiotherapy the metal ions should of course be ions of radioactive isotopes.

However the invention is especially applicable to MR contrast agents and Gd(III) and Dy(III) will generally be the preferred metal ions. Complexes of Gd(III) may be utilized for $T_1$ or $T_2^*$ imaging whereas complexes of Dy(III) are preferred for $T_2^*$ imaging.

As the aryl groups carry protic acid groups, the compounds of the invention may be in protonated non-salt form or in the form of salts with appropriate counterions. For use as diagnostic contrast agents, the salts will be with physiologically tolerable counterions and in this regard particular mention may be made of the inorganic and organic counteranions well known for their tolerability, namely the alkali and alkaline earth metal ions (e.g. Na), ammonium, ethanolamine, diethanolamine and meglumine as well as the counterions of tris buffer.

The compounds of the invention may be prepared using conventional chemical techniques by conjugating together aryl, linker and macrocyclic groups and subsequently introducing or deprotecting functional groups which would inhibit the conjugation procedure, e.g. the coordinating side chains on the macrocycle, the metabolizable groups on the linker and the protic acid groups on the aryl function. In general, while the linker can be conjugated to the aryl or macrocycle end groups simultaneously or consecutively in either order, the linker to aryl conjugation is expediently carried out before the linker to macrocycle conjugation. For this purpose, a bifunctional linker molecule is preferably used, optionally with one end group protected during the first conjugation and deprotected before the second.

Metallation of the chelate moiety can be carried out before or during, but preferably after the construction of the chelant-linker-aryl-acid molecule.

Thus viewed from a further aspect the invention provides a process for the preparation of compounds according to the invention said process comprising at least one of the following steps:

(a) metallating a chelant compound of formula I;

and (b) deprotecting a compound of formula I in which at least one protic acid or metabolizable group is protected by a protecting group.

Methods of complexing metal ions with chelants are known and are within the level of skill in the art. Each of the metals used can be incorporated into a chelant moiety by one of three general methods: direct incorporation, template synthesis and/or transmetallation.

Direct incorporation is preferred. Generally the metal is titrated from sub-stoichiometric levels up to full incorporation, thus eliminating the need for dialysis and extensive chromatographic purification. In this manner significant losses as well as dilution are avoided. Application of the invention to radionuclides with short half-lives may require metallation of the chelant shortly before administration with metallation being followed by simple rapid purification (e.g. gel filtration) to remove excess unbound radionuclide.

The metal ions Fe(III), Cr(III), Mn(II), Hg(II), Pb(II), Bi(III) and the lanthanides can be directly incorporated into the chelants of the invention by the following general procedure. A water-soluble form of the metal, generally an inorganic salt, is dissolved in an appropriate volume of distilled, deionized water. The pH of the solution will be below 7. An aqueous solution containing an equimolar amount of the chelant is added to the metal solution at ambient temperature while stirring. The pH of the mixture is raised slowly by addition of base, typically 0.1M NaOH, until the donor groups of the polychelant are deprotonated, generally in the pH range of 5 to 9, depending on the chelant moieties. Particular care must be taken with the lanthanide ions to maintain the pH below 8 to avoid precipitation of the metal hydroxide. Metal incorporation into DOTA or DO3A derived and related macrocylic chelant moieties will normally be a slow process, as described in the references cited below. Specific examples of the procedure are contained in the following references.

Choppin et al, J. Inorg. Nucl. Chem., 33:127 (1971), Margerum, Rec. Chem. Prog., 24:237 (1973) and D'Olieslager et al, J. Inorg. Nucl. Chem., 35:4255 (1973) describe direct incorporation of the lanthanides into polyaminopolycarboxylates. Margerstadt, Mag. Res. Med., 3:808 (1986) and WO-A-87/06229 describe incorporation of Gd(III) into DOTA. A method of preparing Bi and Pb complexes of DOTA is described by Kumar et al, J. Chem. Soc. Chem. Commun., 3:145 (1989). All references mentioned herein are incorporated herein by reference in their entirety.

Direct incorporation of Hf, Zr, W, Hg and Ta can be performed according to well known methods. See, for example, U.S. Pat. No. 4176173 (Winchell).

Transmetallation is useful when the metal ion needs to be reduced to a more appropriate oxidation state for the donor atoms of the chelant moiety to bind. For example, to incorporate $^{99m}$Tc or $^{186/188}$Re, the metal ion must be reduced to Tc(V) or Re(V) by the use of reducing agents such as $SnCl_2$ or cysteine by well known methods. This method requires formation of an intermediate complex. A typical example is the reduction of $^{99m}$Tc with Sn in the presence of a weakly coordinating ligand such as glucoheptonate prior to complexation with chelants such as DOTA. These methods are well known in the radio pharmaceutical art. $^{67}$Cu utilizes tetra amine chelates such as tet A or tet B (see Bhardaredj et al., JACS, 108:1351 (1986)) to stabilize Cu(II) for reaction with stronger-binding chelants.

For step (b) protection and deprotection may be effected using conventional chemical techniques. Appropriate protecting groups for different chemical groups and the ways in which deprotection may be effected are well known. The reader is referred to "Protective groups in organic synthesis"

by Greene and "Protective groups in organic chemistry" by McOmie, Plenum, 1973.

Thus for example protic acid groups may be protected as ester groups, e.g. $COOCH_3$ or $COOtBu$ groups, and deprotected by acid or base hydrolysis.

By way of example the following synthetic scheme may be followed from known starting products to products according to the invention:

(v = 5 to 15, eg 10)

(2) + $Gd_2O_3$ $\xrightarrow{NaOH}$ Sodium salt of the Gd(III) chelate of (2)

SELECTED EXAMPLES GdDO3A-DOBA

SYNTHESIS OF GdDOTA-DOBA

-continued

COMPLEX
GdDOTA-DOBA

The metal chelates of the chelants of the invention may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.001 to 1.2, e.g. 0.02 to 0.5, mmoles/kg bodyweight while for X-ray applications dosages of from 0.5 to 1.5 mmoles/kg are generally effective to achieve X-ray attenuation. Preferred dosages for most X-ray applications are from 0.8 to 1.2 mmoles of the lanthanide or heavy metal/kg bodyweight.

The compounds of the present invention may be formulated with conventional pharmaceutical or veterinary aids, for example stabilizers, antioxidants, osmolality adjusting agents, buffers, pH adjusting agents, etc., and may be in a form suitable for parenteral administration; for example injection or infusion. Thus the compounds of the present invention may be in conventional pharmaceutical administration forms such as solutions, suspensions or dispersions in physiologically acceptable carrier media, for example water for injections.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (such as, for example, DTPA, DTPA-bisamide or non-complexed chelant of formula I) or calcium chelate complexes (as for example calcium DTPA, CaNaDTPA-BMA, or calcium complexes of compounds of formula I), or, optionally, additions (e.g., 1 to 50 mole percent) of calcium or sodium salts (for example, calcium chloride, calcium ascorbate, calcium gluconate or calcium lactate).

Parenterally administrable forms, e.g., intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Viewed from a further aspect the invention provides a diagnostic or therapeutic composition comprising a compound of the invention or a salt thereof together with at least one pharmaceutical carrier or excipient.

Viewed from a still further aspect the invention provides the use of a compound according to the invention or a salt thereof for the manufacture of a diagnostic or therapeutic composition.

Viewed from another aspect the invention provides a method of generating an image of a human or non-human animal, especially mammalian, body which method comprises administering to said body an image enhancing amount of a compound according to the invention or a salt thereof and thereafter generating an image e.g. an MR, X-ray, ultrasound, or scintigraphic image, of at least a part of said body, especially of the hepatobiliary system.

Viewed from a still further aspect the invention provides a method of therapy of the human or animal body said method comprising administering to said body a therapeutically effective amount of a compound according to the invention.

This invention is further illustrated by the following specific but non-limiting examples (in which temperatures are given in degrees Celsius and concentrations as weight percentages unless otherwise specified) and by the accompanying drawings in which:

EXAMPLE 1

Synthesis of (Tris H$^+$)Gd-DO3A-DOBA i. Synthesis of methyl p-(bromodecyloxy)benzoate

To a suspension of sodium hydride (150 mg, mineral oil dispersion washed with THF, 5 mmol) in THF (25 mL), a solution of p-hydroxymethylbenzoate (761 mg, 5 mmol) in THF (5 mL) was added at 0° C. under nitrogen. The solution was then warmed to ambient temperature. Methanol (5 mL) was added and the solution stirred for 1 hour. A solution of 1,10-dibromodecane (1.5 g; 5 mmol) in THF (5 mL) was added and the mixture was heated at 70° C. for 5 hours. The solution was concentrated, redissolved in chloroform, washed with water and dried ($Na_2SO_4$). The residue was chromatographed on silica gel and the desired product was eluted with 25% $CHCl_3$ in petroleum ether. Yield: 1.77 g (48%). $^1$H NMR ($CDCl_3$) :7.95 (d), 6.87 (d), 3.98 (t), 3.40 (t), 1.80 (m), 1.40 (br), 1.29 (s). $^{13}$C NMR ($CDCl_3$) :162.94, 131.55, 114.04, 68.15, 51.84, 34.01, 32.79, 29.39, 29.32, 29.27, 29.08, 28.71, 28.13, 25.94. FABMS: 371.1 (MH+).

ii. Synthesis of 10-(p-methoxycarbonyl-phenyloxydecyl)-1,4,7,10-tetraazacyclododecane-1,4,7-tri-t-butyl acetate DO3A-tri-t-butyl ester (2.5 g; 4.14 mmol) in DMF (25 mL) was treated with tetramethyl guanidine (1.0 g; 4.8 mmol) and methyl 10-(p-bromodecyloxy)benzoate (1.6 g; 4.3 mmol). After heating at 50° C. for 6 hours, the solvent was distilled off under vacuum at 50° C. The residue was dissolved in $CHCl_3$, washed with water, dried ($Na_2SO_4$) and concentrated to yield the crude product as a yellow oil (4.0 g). $^1$H NMR ($CDCl_3$) :7.91 (d), 7.83 (d), 3.94 (t), 3.82 (s), 3.22 (br), 2.79 (broad), 2.31 (br), 1.72 (m), 1.39 (s), 1.22 (s). $^{13}$C NMR ($CDCl_3$) :171.07, 166.77, 131.43, 122.15, 113.93, 80.49, 68.06, 56.56, 56.14, 52.23, 51.96, 51.90, 51.69, 50.68, 47.53, 29.47, 29.41, 29.24, 28.99, 28.12, 27.83, 27.52, 27.02, 25.87.

iii Synthesis of 10-p-methoxy carbonyl-phenyloxydecyl-1,4,7,10-tetraazacyclododecane-1,4,7-tri-acetic acid The crude product from above (4.0 g), was dissolved in dichloromethane (40 mL) and trifluoroacetic acid (40 mL) was added to the solution. After stirring at ambient temperature for 1 hour, the solution was concentrated and the process repeated four more times. After the final treatment, the solution was concentrated and chased with dichloromethane (five times) and water (four times). The residue was treated with water (100 mL) and allowed to stand overnight when the product separated as a colourless solid. It was filtered and dried in vacuo. Yield: 1.37 g (42%). $^1$H NMR (DMSO-$d_6$): 7.50 (br), 6.61 (br), 4.17 (br), 3.60 (br), 3.39 (br), 3.02 (br), 2.48 (br), 0.89 (br). $^{13}$C NMR (DMSO-$d_6$) : 172.82, 171.34, 164.49, 131.36, 114.52, 67.96, 54.35, 52.37, 51.92, 51.02, 49.01, 48.99, 28.94, 26.15, 25.51, 22.13. FABMS: 637.4 (MH+).

iv. Synthesis of 10-p-carboxy phenyloxydecyl-1,4,7,10-tetraazacyclododecane-1,4,7-tri-acetic acid (DO3A-DOBA)

The crude product from above (1.37 g) was suspended in mixture of water (20 ml) and methanol (30 mL) and treated with KOH (0.47 g). After heating at 50° C. for 9 hours, the solution was concentrated and the residue was loaded on to AGI X-8 ion exchange resin (100–200 mesh, acetate form). The product was eluted with a mixture of 1:1 (v/v) ethanol and 2N ACOH and concentration of the eluate yielded a residue which was suspended in ethanol, filtered and dried under vacuum to obtain a colourless solid. Yield: 0.82 g (61%). $^1$H NMR ($D_2O$):7.62 (d), 6.79 (d), 3.90 (t), 2.86 (br), 2.19 (br), 1.56 (t), 1.07 (br). FABMS:623.4 (MH+). Elemental analysis; calculated for $C_{31}H_{50}N_4O_9 \cdot 1.25\ H_2O$:C 57.70%, H 8.20%, N 8.680%; found:C 57.70%, H 7.86%, N 8.57%.

v. Synthesis of gadolinium complex of 10-p-carboxphenyloxydecyl-1,4,7,10-tetraazacyclododecane-1,4,7-tri-acetic acid (GdDO3A-DOBA)

To a solution of gadolinium acetate in water (40 mL), 10-p-carboxy phenyloxydecyl-1,4,7,10-tetraazacyclododecane-1,4,7-tri-acetic acid (500 mg, 0.8 mmol) was added. The suspension was treated with 1M tris buffer (4.3 mL) to aid the complete dissolution of the ligand. The solution was heated at 40° C. for 4 hours and stirred at ambient temperature overnight. An aliquot was tested for excess gadolinium with xylenol orange and gadolinium acetate was added in 5 mole % increments until the xylenol orange test was positive. Then the ligand was added in 0.5 mole % increments until the xylenol orange test was negative for excess gadolinium. The product was isolated as the tris salt of the gadolinium complex from the reaction mixture by centrifugation. Yield: 670 mg (89%). FABMS:778; (MH+):778. Elemental analysis; calculated for $GdC_{35}H_{58}N_5O_{12}$. 2.5 $H_2O$:C 44.57%, H 6.73%, N 7.43%, Gd 16.67%; found:C 44.97%, H 6.91%, N 7.80%, H 16.28%.

vi. $^{153}$Gd-labeling and formulation of 10-p-carboxyghenyloxydecyl-1,4,7,10-tetraazacyclododecane-1,4,7-tri-acetic acid ($^{153}$GdDO3A-DOBA)

Radiolabeling of the ligand (97 mg) was carried out using $^{153}$GdCl$_3$ and 400 mole % of tris. After the incorporation of the label (as shown by TLC, HPLC) stoichiometric amount of the cold carrier (i.e. GdCl$_3$) was added to complete the complexation which had to be carried out at a pH of 5.47 to avoid the formation of a gel-like precipitate. The formulation (10 mM) was completed after making the necessary osmolality and pH adjustments. The final formulation was assayed for purity (TLC 99.8%, HPLC 99.6%), excess Gd (negative xylenol orange test) and specific activity (6.3 μCi/mL).

The biodistribution study was performed in male Swiss-Webster mice (weighing 25–27 g) by injecting the labeled material at a dose of 0.1 mmol/kg and measuring the radioactivity in blood, liver, spleen, heart, kidneys, gut content, gut and carcass at time points 3 min, 9 min, 15 min, 1 hour, 4 hours and 24 hours, using two mice at each time point. Urine and faeces were also collected at 4 and 24 hours and counted for radioactivity.

EXAMPLE 2

Synthesis of DTPA-bis(10-p-carboxyphenyloxydecylamide) and its gadolinium complex -continued i. Synthesis of methyl 10-(p-aminodecyloxy)benzoate Methyl 10-(p-bromodecyloxy)benzoate (1.6 g; 4.3 mmol) is dissolved in acetonitrile and treated with sodium azide mice per time point were euthanized and the organs were counted for radioactivity. The biodistribution and excretion data determined for this compound are set out in Table I.

TABLE I

| | | | | | GdDO3A-DOBA biodistribution and excretion | | | | |
|---|---|---|---|---|---|---|---|---|---|
| | 1 time (min) | 2 blood* | 3 liver | 4 kidneys | 5 gut | 6 gut contents | 7 carcass | 8 urine + wash | 9 feces |
| 1 | 3 | 19.63 | 29.81 | 1.62 | 3.85 | 0.53 | 41.79 | | |
| 2 | 9 | 5.76 | 53.7 | 0.84 | 1.19 | 1.68 | 24.71 | | |
| 3 | 15 | 5.56 | 57.84 | 0.72 | 2.36 | 1.48 | 22.86 | | |
| 4 | 60 | 3.01 | 56.41 | 0.47 | 6.75 | 8.1 | 9.74 | | |
| 5 | 240 | 2.52 | 35.08 | 0.66 | 5.85 | 23.33 | 5.95 | 12.62 | 0.18 |
| 6 | 1440 | 0.03 | 4.82 | 0.09 | 0.1 | 0.56 | 0.71 | 5.6 | 56.98 |

*numerical values in colums 2 to 9 are % of injected dose.

(0.65 g; 10 mmol). The solution is refluxed for 4 hours under nitrogen, filtered and concentrated. The crude azide is purified by column chromatography on silica gel. The crude product is dissolved in ethanol (10 mL) and treated with 10% Pd on carbon (10 weight %) and hydrogenated using a Paar hydrogenator at a hydrogen pressure of 50 psi. The solution is then filtered through celite and concentrated. The crude product is purified by column chromatography on silica gel.

ii. Synthesis of sodium 10-(p-aminodecyloxy)benzoate

The product obtained from above (1.0 g; 3.3 mmol) is dissolved in methanol (5 mL) and treated with sodium hydroxide (1M, 10 mL). The solution is refluxed for 2 hours and concentrated. The residue is treated with DTPA-bis (anhydride) (0.59 g; 1.65 mmol) and stirred at ambient temperature overnight. The desired product is isolated by ion exchange chromatography on AG1 X-8 ion exchange resin.

iii. Synthesis of gadolinium DTPA-bis(10-p-carboxyphenyloxydecylamide)

The ligand obtained from above (1.0 g; 1.03 mmol) is treated with gadolinium acetate (0.34 g; 1.03 mmol) and the mixture is stirred at ambient temperature for 2 hours. The gadolinium titer is monitored by xylenol orange test. After completion of metal incorporation, the solution is concentrated and chased with water to remove acetic acid formed in the reaction and the product is dried under vacuum.

EXAMPLE 3

GdDO3A-DOBA biodistribution and excretion

Figure 1:
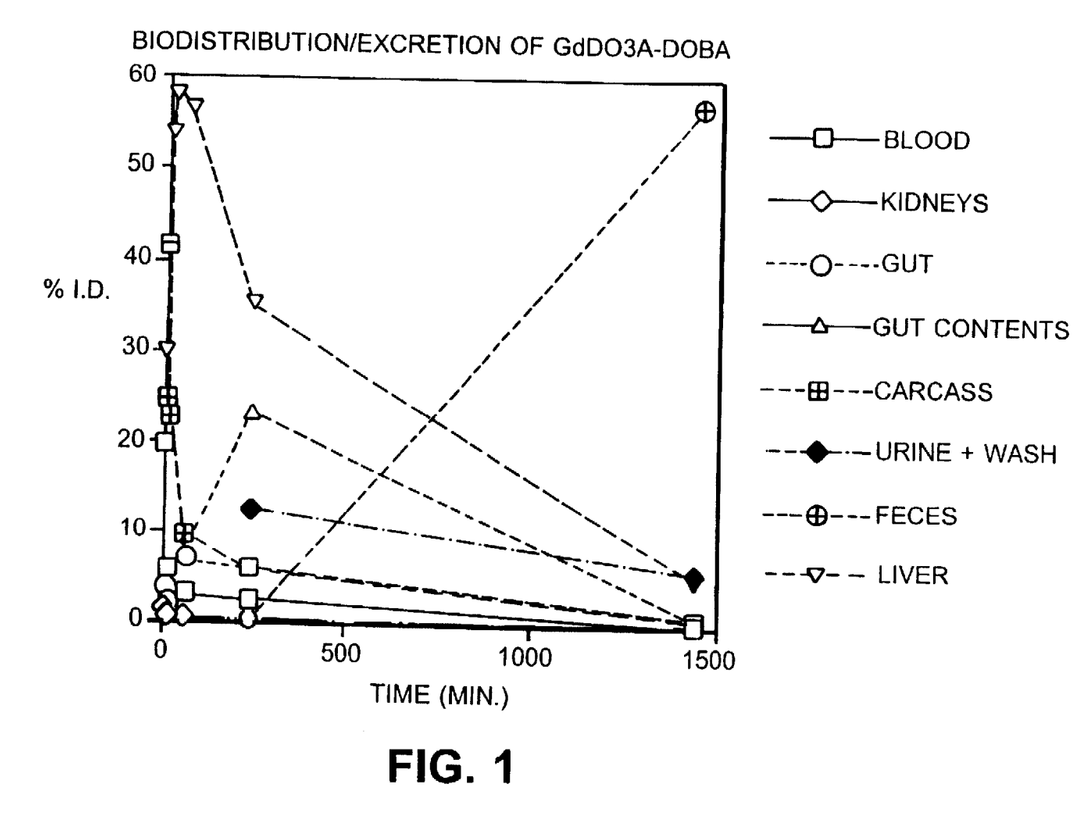
FIG. 1 is a plot of the biodistribution and excretion characteristics of one compound according to the invention, administered to mice.

A formulation of $^{153}$Gd-labelled DO3A-DOBA (prepared as the sodium salt analogously to Example 1 using $^{153}$Gd$_2$O$_3$) was injected into male Swiss-Webster mice. Two From Table I it is clear that even at 3 minutes post-injection there is rapid uptake of the labelled material to the extent of 30% into the liver. This amount increases to 54, 58 and 58% over a period of 9, 15 and 60 minutes and then decreases to 35 and 5% over 4 and 24 hours respectively. This indicates that the compound has an extremely favourable liver profile with high uptake which remains over an hour thus providing a favourable imaging window. The uptake of the material in gut and gut content increases with time (i.e. from 3 minutes to four hours) and the material is virtually cleared in 24 hours indicating typical biliary clearance which is further substantiated by the recover of the activity (57% of the injected dose) in the feces, 24 hours post injection. Uptake in the kidneys is relatively low, and the renal clearance is 13% after 4 hours (urine+cage wash) and 6% after 24 hours (urine+cage wash). The distribution and clearance data is presented in graphical form in FIG. 1.

EXAMPLE 4

Gd DO3A-DOBA and Gd EOB-DTPA—
Comparison of liver uptake and clearance

Using injections into male Swiss-Webster mice and animal tissue sampling as in Example 2, comparative results were generated for Gd-EOB-DTPA using $^{153}$Gd labelled material for biodistribution. FIG. 2 presents the liver uptake profiles of Gd-DO3A-DOBA and Gd-EOB-DTPA. It is clear from this Figure that Gd DO3A-DOBA accumulates to a higher extent (58%) and persists longer thus providing a better imaging window. The uptake of Gd-EOB-DTPA in liver is less (<40%) and it clears relatively rapidly.

EXAMPLE 5

Synthesis of GdDOTA-DOBA (i) Synthesis of methyl p-(10-bromodecyloxy)benzoate

A mixture of 1,10-dibromodecane (18.01 g, 60 mmol), methyl p-hydroxy benzoate (9.12 g, 60 mmol) and $K_2CO_3$ (8.28 g, 60 mmol) in acetone (90 mL) was stirred at reflux for 20 hours. The white solid was filtered off and washed with acetone. The filtrate and washings were combined and concentrated to a white solid from which the desired product was isolated by column chromatography on silica gel using hexane/chloroform solvent gradient for elution (10.8 g, 48.4%). $^1$H NMR (CDCl$_3$, δ): 7.95 (d), 6.88 (d), 3.98 (t) 3.85 (s), 3.39 (t), 1.80 (m), 1.52 (m), 1.42 (m) and 1.29 (m). FABMS: 371 (MH+).

(ii) Synthesis of methyl p-(10-N-phthalimidodecyloxy)-benzoate

A mixture of methyl p-(10-bromodecyloxy)benzoate (10.44 g, 28.12 mmol) and potassium phthalimide (5.47 g, 29.53 mmol) in anhydrous DMF (175 mL) was stirred at 60° C. for 14 hours under nitrogen. The solvent was removed under vacuum and the residue was dissolved in CHCl$_3$ and washed with water (4×15 mL). The aqueous washings were combined and back-extracted once with CHCl$_3$ (100 mL). The combined organic layers were dried with MgSO$_4$ and the solution was concentrated to yield the crude product which was purified by chromatography on silica gel using hexane/chloroform solvent gradient for elution (11.8 g, 96%). $^1$H NMR (CDCl$_3$, δ): 7.95 (d), 7.81 (m), 7.68 (m), 6.86 (d), 3.97(t), 3.85 (s), 3.64 (t), 1.76 (m), 1.65 (m), 1.54 (m), 1.42 (m), 1.29 (m). FABMS: 438 (MH+).

(iii) Synthesis of methyl p-(10-aminodecyloxy)benzoate

Methyl p-(10-N-phthalimidodecyloxy)benzoate (8.52 g, 19.48 mmol) was dissolved in methanol (75 mL) at 65° C. Hydrazine monohydrate (1 mL, 20.62 mmol) was added and the solution refluxed under nitrogen for 22 hours. The solution was cooled to ambient temperature and the precipitate was filtered. The solution was concentrated and the residue was combined with the precipitate and treated with chloroform (500 mL). The solution was washed with water and the washings back extracted with chloroform (2×100 mL). The combined organic layer was dried over MgSO$_4$ and concentrated to yield the product (5.62 g, 97%). $^1$H NMR (CDCl$_3$, δ): 7.95 (d), 6.88 (d), 3.97 (t), 3.86 (s), 2.64 (t), 1.78 (m), 1.53 (m), 1.43 (m), 1.28 (m).

(iv) Synthesis of methyl-p-(10-chloroacetamidodecyloxy)-benzoate

The crude product from (iii) above (5.62 g, 18.84 mmol) and triethylamine (2.6 mL, 18.7 mmol) were dissolved in chloroform (90 mL) and cooled in an ice bath. A solution of chloroacetyl chloride (1.5 mL) in chloroform (40 mL) was added dropwise with stirring. After the completion of the addition, the solution was stirred in the ice bath for 15 minutes and warmed to ambient temperature and stirred for 20 hours. The solution was washed with water (4×80 mL). Drying (MgSO$_4$) and concentration yielded the product (6.71 g, 93%) which was used without further purification. $^1$H NMR (CDCl$_3$, δ): 7.95 (d), 6.87 (d), 6.54 s, br), 4.01 (d), 3.96 (t), 3.86 (s), 3.28 (q), 1.76 (m), 1.55 (m), 1.45 (m), 1.29 (m). $^{13}$C NMR (CDCl$_3$, δ): 130.71, 130.66, 121.52, 113.23, 75.37, 67.33, 50.95, 41.85, 39.04, 28.56, 28.53, 28.47, 28.43, 28.33, 28.25, 25.94, 25.11.

(v) Synthesis of 10-(p-methoxycarbonyl-phenyloxydecylcarbamoylmethyl)-1,4,7,10-tetraazacyclododecane-1,4,7-tri-t-butyl acetate DO3A-tri-t-butyl ester (9.31 g, 15.63 mmol) and triethylamine were dissolved in DMF (90 mL) and the chloroacetamide from (iv) above (6.0 g, 15.63 mmol) was added to the solution which was heated at 60° C. under nitrogen for 19 hours. The solvent was removed under vacuum and the residue taken up in chloroform (200 mL). The solution was washed with water (3×100 mL), dried over MgSO$_4$ and concentrated to yield the crude product (10.97 g) as an oil.

(DO3A 1,4,7-Triscarboxymethyl-1,4,7,10-tetraazacyclododecane).

EXAMPLES 6–14

Using the following reaction scheme, analogs of DO3A-DOBA (the compound of Example I) were prepared (where $R^{11}$ is halogen, eg. Br; $X^{11}$ is $CH_2$ or O; and p is a positive integer).

The synthesis of the compounds of Examples 6 to 14 was straightforward and reproducible in all cases.

| Example No. | —L—Ar(AH)$_n$ | | Short Name |
|---|---|---|---|
| 6 | (CH$_2$)$_{10}$ | O-m-carboxyphenyl | DO3A-DOmBA |
| 7 | (CH$_2$)$_{10}$ | O-o-carboxyphenyl | DO3A-DOoBA |

21
-continued

| Example No. | —L—Ar(AH)$_n$ | Short Name |
|---|---|---|
| 8 | (CH$_2$)$_{10}$-O-3,5-bis carboxyphenyl | DO3A-DOIA |
| 9 | (CH$_2$)$_6$-O-p-carboxyphenyl | DO3A-HOBA |
| 10 | (CH$_2$)$_8$-O-p-carboxyphenyl | DO3A-OOBA |
| 11 | (CH$_2$)$_2$O(CH$_2$)$_7$-O-p-carboxyphenyl | DO3A-2 (O$^{3,11}$)BA |

22
-continued

| Example No. | —L—Ar(AH)$_n$ | Short Name |
|---|---|---|
| 12 | (CH$_2$)$_7$O(CH$_2$)$_2$-O-p-carboxyphenyl | DO3A-2 (O$^{8,11}$)BA |
| 13 | (CH$_2$CH$_2$O)$_4$ p-carboxyphenyl | DO3A-4 (O) BA |
| 14 | (CH$_2$CH$_2$O)$_4$ 3,5 bis carboxyphenyl | DO3A-4 (O) IPA |

The linker groups for the compounds of Examples 11 to 14 were synthesized using the following schemes.

Synthesis of the linker for DO3A-2(O $^{8,11}$)BA

Synthesis of the linker for DO3A-2(O $^{3,11}$)BA

Synthesis of linker for DO3A-4(O)BA

-continued
Synthesis of linker for DO3A-4(O)IPA

EXAMPLE 15

Product Physicochemical Characteristics

Elemental Analysis

Quantitative elemental analysis was performed on the ligands and complexes. Satisfactory agreement between the observed values for carbon, hydrogen and nitrogen and the corresponding values calculated on the basis of molecules containing associated water (approximately 0–3) was observed.

Mass spectroscopy

Satisfactory fast atom bombardment mass spectra were obtained for the complexes and ligands. The m/e values for the parent ion MH+ agreed well with those calculated. The gadolinium isotopic distribution pattern was indicative of the presence of one gadolinium ion in the complexes.

NMR Spectroscopy

The ligands were characterised by one dimensional $^1$H and $^{13}$C NMR spectroscopy. The results were consistent with the structure of the ligands.

Appearance

The metal chelates were isolated as fine white or off-white powders.

Thermal Stability

The thermal stability of GdDO3A-DOIA as the ammonium salt was examined by means of thermogravimetric analysis. The curve suggests that loss of surface associated and bound water (6.9 weight %) occurred over the range of 25°–175° C. and loss of ammonia (9.3 weight %) occurred over the range of 175°–325° C. Above 350° C. general decomposition of the complex took place.

Partition Coefficients

The partition coefficients for the distribution of the gadolinium chelates in n-butanol/tris buffer (pH 7.4) phases were measured by the minimal sample method. After shaking to effect partitioning and phase separation, the concentration of the chelate in each phase was indirectly determined by measuring Gd concentration by ICP/AES. The logP values are given in Table II below.

TABLE II

Partition coefficients for the distribution of Gd chelates in n-butanol/tris buffer (pH 7.4) phases

| Ligand | L | ArAH | Relaxivity[a] $r_1$ (mMs)$^{-1}$ | logP |
|---|---|---|---|---|
| DO3A-DOBA (Example 1) | $C_{10}H_{20}$ | —O—C$_6$H$_4$—COO Na$^+$ (para) | 7.3 ± 0.3 (W) 10.2 ± 0.2 (S) | −0.16 |
| DO3A-DOIA | $C_{10}H_{20}$ | —O—C$_6$H$_4$(COO Na$^+$)$_2$ (3,5-disubstituted) | 12.3 ± 0.4 (W) 7.0 ± 0.2 (S) | −1.1 |
| DO3A-DOmBA | $C_{10}H_{20}$ | —O—C$_6$H$_4$—COO Na$^+$ (meta) | 10.3 ± 0.2 (W) 9.8 ± 0.1 (S) | 0.58 |
| DO3A-DOoBA | $C_{10}H_{20}$ | Na$^+$OOC—C$_6$H$_4$—O— (ortho) | 7.6 ± 0.5 (W) 16.6 ± 0.9 (S) | 0.27 |

TABLE II-continued

Partition coefficients for the distribution of
Gd chelates in n-butanol/tris buffer (pH 7.4) phases

| Ligand | L | ArAH | Relaxivity[a] $r_1$ (mMs)$^{-1}$ | logP |
|---|---|---|---|---|
| DO3A-HOBA | $C_6H_{12}$ |  | 3.3 ± 0.1 (W) <br> 7.7 ± 0.3 (S) | −1.9 |
| DO3A-OOBA | $C_8H_{16}$ |  | 7.1 ± 0.1 (W) | −0.71 |
| DO3A-2(O$^{3,11}$)BA | $C_2H_4-$ <br> $OC_7H_{14}$ |  | 4.9 ± 0.0 (W) <br> 10.3 ± 0.2 (S) | −1.1 |
| DO3A-2(O$^{8,11}$)BA | $C_7H_{14}-$ <br> $OC_2H_4$ |  | 5.1 ± 0.0 (W) <br> 7.0 ± 0.2 (S) | −0.8 |
| DO3A-4(O)BA | $C_2H_4-$ <br> $(OC_2H_4)_3$ |  | 3.4 ± 0.0 (W) <br> 4.2 ± 0.1 (S) | <−2.0 |
| DO3A-4(O)IPA | $C_2H_4-$ <br> $(OC_3H_4)_3$ |  | 3.5 ± 0.0 (W) <br> 4.2 ± 0.0 (S) | −1.7 |

[a]relaxivity at 20 MHz and 37° C. in water (W) and Seranorm (S)

Relaxivity

Longitudinal ($r_1$) and transverse ($r_2$) molar relaxivities were derived from the relaxation time data ($T_1$ or $T_2$) of water protons at various concentrations of the chelates at 20 MHz and 37° C. These measurements were carried out both in water and Seronorm (an in vitro matrix model used to simulate in vivo conditions).

EXAMPLE 16

Biological Characterisation

Biodistribution, Elimination and Whole Body Autoradiography (Mice)

The distribution of the gadolinium complexes in selected tissues and organs at various time points was evaluated after the intravenous administration of 153 Gd-labeled compounds in young male Swiss-Webster mice. The radiolabeled formulations were made at a concentration of either 10 or 5 mM Gd (depending on the solubility of the chelates) and administered intravenously at a dosage of 0.1 mmol/kg body weight. Groups of two mice were sacrificed at 3, 9, 15 and 60 minutes and 24 hours post injection. Radioactivity was measured in blood, liver, heart, spleen, lungs, brain, kidneys and other organs of interest. In addition, urine and feces were collected at 2, 4 and 24 hours. In the case of DO3A-DOBA and EOB-DTPA additional time points (30 minutes, 2 hours, 2 days and 7 days) were considered for extended distribution profile. Based on the radioactivity measured, the tissue distribution was expressed as the percent of the administered dose remaining in each tissue. The biodistribution in liver and kidneys and the elimination in urine and feces for the gadolinium complexes are listed in Table III below. The uptake increased steadily during 9 and 15 minutes (42.85–78.56%), and slowly decreased over 60 minutes. However, even at 60 minutes there is considerable level of the injected dose remaining in the liver. The liver clearance occurred gradually over 4 hours. After 24 hours, only a small amount (0.89–6.69% I.D.) remained in the liver. As compared to GdEOB-DTPA, the compounds listed below had much higher liver uptake, with a substantially high proportion of the injected dose remaining in the liver between 0–60 minutes (i.e. giving a longer imaging window).

TABLE III

Biodistribution and Elimination of Gd complexes

| Ligand | L | ArAH | Liver uptake % i.d | Liver retn. (24 h) % i.d. |
|---|---|---|---|---|
| D03A-D0BA | $C_{10}H_{20}$ | $-O-\text{C}_6H_4-COO^-Na^+$ (para) | 70.03 (30 min) | 4.82 |
| D03A-D01A | $C_{10}H_{20}$ | $-O-\text{C}_6H_3(COO^-Na^+)_2$ (1,2-diCOO) | 71.37 (9 min) | 2.34 |
| D03A-D0$_m$BA | $C_{10}H_{20}$ | $-O-\text{C}_6H_4-COO^-Na^+$ (meta) | 65.11 (15 min) | 4.64 |
| D03A-D0$_o$BA | $C_{10}H_{20}$ | $-O-\text{C}_6H_4-COO^-Na^+$ (ortho) | 61.97 (15 min) | 2.73 |
| D03A-HOBA | $C_6H_{12}$ | $-O-\text{C}_6H_4-COO^-Na^+$ | 42.85 (15 min) | 2.98 |
| D03A-OOBA | $C_8H_{16}$ | $-O-\text{C}_6H_4-COO^-Na^+$ | 65.06 (15 min) | 6.69 |
| D03A-2(O$^{3,11}$)BA | $C_2H_4-OC_7H_{14}$ | $-O-\text{C}_6H_4-COO^-Na^+$ | 75.56 (15 min) | 0.91 |
| D03A-2(O$^{8,11}$)BA | $C_7H_{14}-OC_2H_4$ | $-O-\text{C}_6H_4-COO^-Na^+$ | 68.79 (9 min) | 4.74 |

The high liver uptake of the compounds listed above was reflected in the low kidney uptake and retention. Correspondingly a lower amount of the activity was recovered in the urine. The amount recovered in the faeces is high, indicating the clearance by hepatobiliary route. This is also supported by the uptake in the gut and gut contents over 4 hours. Thus these compounds were taken up predominantly by liver and cleared by the hepatobiliary route with the kidney uptake and renal clearance being the secondary route.

The whole body autoradiography (WBA) was performed in two male Swiss-Webster mice that received a single i.v. administration of 10 mL/kg (equivalent to 63 μci/kg) of $^{153}$GdDO3A-DOBA (specific concentration: 6.3 μci/mL). Four hours and 7 days post injection each mouse was euthanized and frozen. Equivalent freeze-dried sections from each mouse were exposed on X-ray films. with 14C standards co-exposed to serve as visual comparison.

The WBA study showed a strong uptake of the label in liver, gall bladder and fecal matter at 4 hours while the stomach contents showed no uptake. For the kidneys, the collecting ducts exhibited high levels of activity while the level was low in the cortex. At 7 days radioactivity was visible at reduced levels in the liver and periosteal regions of the bone. The liver showed highest retention of the radioactivity at 7 days as compared to other tissues such as the kidneys, gall bladder and intestines. No specific uptake was seen in brain parenchyma. Excretion of the material through the bile in to the gut and feces was evident with the kidneys appearing as the second route of excretion. These results are in agreement with the biodistribution studies, and suggest specific hepatocellular rather than RES uptake by the liver. The rapid blood clearance of the complex is also demonstrated.

We claim:

1. A compound of formula I where Ch is an aminopolycarboxylic acid chelant or a phosphorus oxyacid analogue thereof; each L is an optionally oxo substituted $C_{2-25}$-alkylene linker wherein at least one $CH_2$ moiety is replaced by a group $X^1$ and wherein L is optionally interrupted by a metabolizable group M but with the provisos that the terminal portion of L which is adjacent to Ch is a $CH_2$ group and that the terminal portion of L which is adjacent to Ar is $X^1$, $-X^1-CH_2-$ or $-X^1-CH_2-CH_2-$; each Ar is an aryl ring optionally substituted by or having fused thereto a further aryl ring; each AH is a protic acid group or a salt thereof, each $X^1$ is O, S, $NR^1$ or $PR^1$; each $R^1$ is hydrogen, alkyl or aryl; and m and n are positive integers; or a salt or chelate thereof.

2. A compound as claimed in claim 1 wherein Ch is a group of formula or where each $X^2$ is O, S or $NR^3$;

each $R^2$ is a bond to a group L, a hydrogen atom or a hydroxyalkyl group;

each $R^3$ is a hydroxyalkyl group, a group $CHR^4AH$, a group $CH_2AR^4$ or a bond to a group L, at least two $R^3$ being groups $CR^4{}_2AH$;

each $R^4$ is a hydrogen atom or a bond to a group L;

each p is 1, 2, 3 or 4;

q is 3 to 8;

v is 0 to 6;

and at least one $R^2$, $R^3$ or $R^4$ is a bond to a group L.

3. A compound as claimed in claim 1 wherein Ch is a macrocyclic polyazacycloalkane group having a skeleton selected from the group consisting of 4. A compound as claimed in claim 1 wherein Ch is a group of formula where each $R^4$ is a hydrogen atom or a bond to a group L, at least one $R^4$ is a bond to a group L, and each $AR^4$ group is an amide, or a salt or chelate thereof.

5. A compound as claimed in claim 1 wherein Ch is a 4,7,10-triscarboxymethyl-1,4,7,10-tetraazacyclododec-1-yl group or a salt or chelate thereof.

6. A compound as claimed in claim 1 wherein Ar is monocyclic and L is a chain $(CH_2)_sX^1$ wherein s is an integer having a value of at least 6 optionally attached to Ch via a $CH_2CONR^1$ group.

7. A compound as claimed in claim 1 wherein Ar is bicyclic and L is a 2 to 20 atom chain terminating at one end with $CH_2$ and at the other with $X^1$ and optionally interrupted by a group M selected from amide, ester, carbamate, acetal, ketal, disulphide, carbonate and esters of phosphorus or sulphur oxyacids.

8. A compound as claimed in claim 1 wherein L is selected from the group consisting of $-(CH_2CONR^1)_z-(CH_2)_dX^1-$
$-(CH_2CONR^1)_z-CH_2CH_2-(X^1CH_2CH_2)_e-$
$-(CH_2CONR^1)_z-(CH_2CH_2X^1)_h-$
$-(CH_2CONR^1)_z-(CH_2)_gCONH\ (CH_2)_fX^1-$
$-(CH_2CONR^1)_z-(CH_2)_gCOONH(CH_2)_fX^1-$
$-(CH_2CONR^1)_z-(CH_2)_g-O(CO)O(CH_2)_fX^1-$
$-(CH_2CONR^1)_z-(CH_2)_gCOO\ (CH_2)_fX^1-$
$-(CH_2CONR^1)_z-(CH_2)_gNHCO\ (CH_2)_fX^1-$
$-(CH_2CONR^1)_z-(CH_2)_gNHOCO\ (CH_2)_fX^1-$
$-(CH_2CONR^1)_z-(CH_2)_gOCO(CH_2)_fX^1-$
$-(CH_2CONR^1)_z-(CH_2)_gOCR^1HO\ (CH_2)_fX^1-$ and
$-(CH_2CONR^1)_z-(CH_2)_gOCR^1{}_2O(CH_2)_fX^1-$ wherein z is 0 or 1, d is 1 to 15 where Ar is bicyclic and 7 to 15 where Ar is monocyclic, e is 1 to 6, h is 2 to 7, f is 1 to 12 and g is 1 to 4.

9. A compound as claimed in claim 8 wherein L is $-(CH_2)_dX^1-$ or $CH_2CONR^1(CH_2)_dX^1$.

10. A compound as claimed in claim 1 wherein the protic AH groups present on the Ar groups are COOH, $SO_3H$, $PO_3H_2$ or $PO_2H$.

11. A compound as claimed in claim 1 wherein Ch is metallated.

12. A compound as claimed in claim 11 wherein Ch is metallated with a paramagnetic metal ion.

13. A diagnostic or therapeutic composition comprising a compound of formula I as defined in claim 1 or a chelate or salt thereof together with at least one pharmaceutical carrier or excipient.

14. A process for the preparation of a compound as claimed in claim 11 said process comprising the following steps:

(a) metallating the chelant compound of formula I; and (b) optionally deprotecting a compound of formula I in which at least one protic acid or metabolizable group is protected by a protecting group.

15. A method of generating an image of a human or non-human animal body which method comprises administering to said body an image enhancing amount of a compound as claimed in claim 11 or a salt thereof and hereafter generating an image of at least a part of said body.

16. A method as claimed in claim 15 wherein said image is an MR image of the hepatobiliary system of said body.

17. A method of therapy of the human or animal body said method comprising administering to said body a therapeutically effective amount of a compound as claimed in claim 1 complexed with a therapeutic metal.

* * * * *